United States Patent [19]

Burdeska

[11] Patent Number: 5,182,389
[45] Date of Patent: Jan. 26, 1993

[54] PROCESS FOR THE PREPARATION OF 2-(2',4'-DIHYDROXYPHENYL)-4,6-DIARYL-S-TRIAZINES

[75] Inventor: Kurt Burdeska, Basel, Switzerland

[73] Assignee: Ciba-Geigy Corporation, Ardsley, N.Y.

[21] Appl. No.: 828,053

[22] Filed: Jan. 30, 1992

[30] Foreign Application Priority Data

Jan. 31, 1991 [CH] Switzerland .............. 291/91
Sep. 23, 1991 [CH] Switzerland .............. 2788/91

[51] Int. Cl.$^5$ .............................. C07D 251/22
[52] U.S. Cl. .............................. 544/219
[58] Field of Search .............................. 544/219

[56] References Cited

U.S. PATENT DOCUMENTS 2,691,018 10/1954 Joyce et al. .............. 544/217
5,084,570 1/1992 Burdeska et al. .............. 544/216

FOREIGN PATENT DOCUMENTS 0395938 11/1990 European Pat. Off. .

OTHER PUBLICATIONS

A. Pinner, Chem. Ber. 23, 2919(1890).

Primary Examiner—John M. Ford
Attorney, Agent, or Firm—Kevin T. Mansfield; Edward McC. Roberts

[57] ABSTRACT

There is disclosed a process for the preparation of 2-(2', 4'-dihydroxyphenyl)-4,6-diaryl-s-triazines of formula

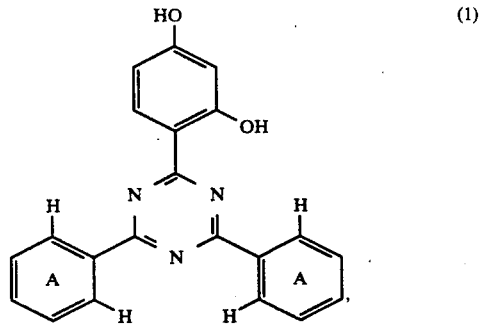

which comprises reacting 2-hydroxy-4,6-diaryl-s-triazines of formula

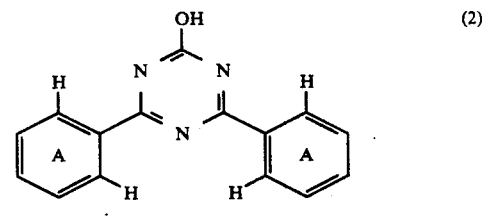

in the temperature range from 100°–150° C. with thionyl chloride in the presence of a catalytic amount of a polar solvent, and subsequently reacting the chloro-s-triazine intermediate with 1,3-dihydroxybenzene using a Lewis acid in the presence of an inert organic solvent, in which formulae (1) and (2) above the rings A may be further substituted by halogen, hydroxy, lower alkyl, lower alkoxy or lower alkoxycarbonyl.

The process of the invention makes it possible to prepare in simple manner and in good yield 2-(2',4'-dihydroxphenyl)-4,6-diaryl-s-triazines which find utility as UV absorbers or as starting materials of the preparation of UV absorbers.

7 Claims, No Drawings

PROCESS FOR THE PREPARATION OF 2-(2',4'-DIHYDROXYPHENYL)-4,6-DIARYL-S-TRIAZINES

The present invention relates to a novel simplified process for the preparation of 2-(2',4'-dihydroxyphenyl)-4,6-diaryl-s-triazines from 2-hydroxy-4,6-diaryl-s-triazines.

The reaction of 2-hydroxy-4,6-diaryl-s-triazines with thionyl chloride to give 2-chloro-4,6-diaryl-s-triazines is disclosed, inter alia, in U.S. Pat. No. 2,691,018.

It has now been found that 2-(2',4'-dihydroxyphenyl)-4,6-diaryl-s-triazines can be prepared in a single step by reacting 2-hydroxy-4,6-diaryl-s-triazines with thionyl chloride and 1,3-dihydroxybenzene without isolation of the chloro-s-triazine intermediate.

Accordingly, the invention relates to a process for the preparation of 2-(2',4'-dihydroxyphenyl)-4,6-diaryl-s-triazines of formula

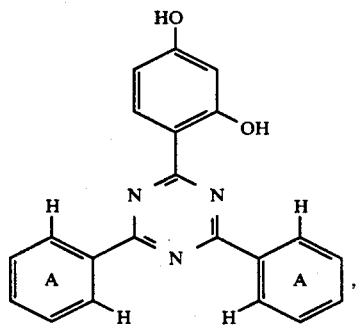
(1)

which comprises reacting 2-hydroxy-4,6-diaryl-s-triazines of formula

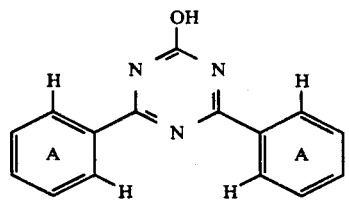
(2)

in the temperature range from 100°-150° C. with thionyl chloride in the presence of a catalytic amount of a polar solvent, and subsequently reacting the chloro-s-triazine intermediate with 1,3-dihydroxybenzene using a Lewis acid in the presence of an inert organic solvent, in which formulae (1) and (2) above the rings A may be further substituted by halogen, hydroxy, lower alkyl, lower alkoxy or lower alkoxycarbonyl.

Lower alkyl and lower alkoxy in the definition of the substituents of the rings A of the compounds of formulae (1) and (2) denote those groups or moieties which contain 1 to 5, preferably 1 to 3, carbon atoms. Such groups are typically methyl, ethyl, n-propyl, isopropyl, n-butyl, sec-butyl, tert-butyl, amyl, isoamyl or tert-amyl and, respectively, methoxy, ethoxy, isopropoxy, isobutoxy or tert-butoxy.

Halogen is fluoro, bromo and, preferably, chloro.

Preferred compounds of formulae (1) and (2) are suitably those in which the rings A are not further substituted.

Lewis acids are compounds having a deficiency in electrons or Broenstedt acids like HCl, HBr etc.

To prepare the compounds of formula I it is preferred to use anhydrous aluminium chloride as Lewis acid.

The reaction of the compound of formula (2) with thionyl chloride and 1,3-dihydroxybenzene is carried out in organic medium. The organic medium is suitably selected from various solvents which must meet the sole condition that they are inert under the reaction conditions. Suitable solvents include: aromatic and aliphatic hydrocarbons and the alkylated, halogenated and nitrated derivatives thereof, typically nitrobenzene, chlorobenzene, o-dichlorobenzene, 1,2,3-trimethylbenzene, toluene, xylene, mixtures of xylene isomers, tetrahydronaphthalene, α-chloronaphthalene, acetylene tetrachloride, ethylene dichloride and the like.

The preferred solvents for the reaction are toluene, xylene or mixtures of xylene isomers.

In addition to the inert organic solvent, a polar organic solvent which has a boiling point in the range from 120° to 150° C. is also used in the first reaction step for the reaction with thionyl chloride. It is preferred to use dimethyl formamide as polar organic solvent, which has the advantage that only a minor excess of thionyl chloride of about 10–15% need be used for the reaction. If this polar solvent is dispersed with, then the reaction has to be carried out with a more than three-fold excess of thionyl chloride, as described in U.S. Pat. No. 2,691,018.

Preferred reactions are those in which the solvent is xylene or a mixture of xylene isomers and dimethyl formamide.

A preferred embodiment of the process of this intention comprises reaction 2-hydroxy-4,6-diphenyl-s-triazine with thionyl chloride in the presence of a catalytic amount of dimethyl formamide, and subsequently reacting the chloro-s-triazine intermediate with 1,3-dihydroxybenzene using aluminium chloride in the presence of toluene, xylene or a mixture of xylene isomers.

The inventive process affords the further possibility of discontinuing the reaction after the reaction of the starting command of formula (2) with thionyl chloride, and isolating the intermediate without much effort. In this case, compounds of formula

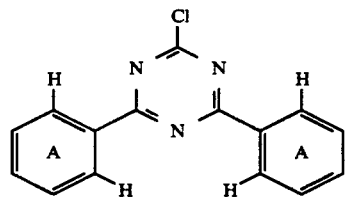
(3)

wherein A is as defined in formulae (1) and (2), are obtained in good yield.

The invention further relates to the preparation of the starting compounds of formula (2).

The process for the preparation of 2-hydroxy-4,6-diaryl-s-triazines of formula (2) comprises reacting an aqueous alkaline solution of a benzamidine hydrohalide in the temperatures range from 0° to 80° C. with an alkyl formate to an alkyl benzimidoylcarbamate, adding an inert organic solvent to the resultant emulsion, and reacting the organic phase containing the alkyl benzimidoylcarbamate to give the 2-hydroxy-4,6-diaryl-s-triazine according to the reaction scheme

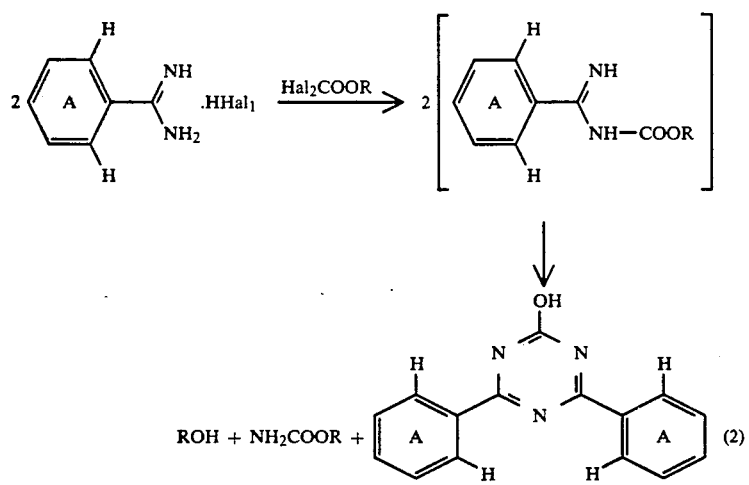

wherein Hal₁ and Hal₂ are halogen and R is C₁–C₄alkyl, and A is as previously defined.

R as C₁–C₄alkyl is methyl, ethyl, propyl, isopropyl, butyl, sec-butyl or tert-butyl. The preferred meaning is ethyl.

The ring closure to give the 2-hydroxy-4,6-diphenyl-s-triazine is also conveniently carried out under a reduced pressure of 150–200 mbar for rapid removal of the alcohol and urethane.

The benzamidine hydrohalide is suitably benzamidine hydrobromide and, preferably, benzamidine hydrochloride.

Preferred alkyl formates are ethyl bromoformate and, more particularly, ethyl chloroformate.

The aqueous alkaline benzamidine hydrohalide solution is preferably an alkali metal hydroxide solution, most preferably a sodium hydroxide solution.

The reaction of the ethyl benzimidoylcarbamate to the compound of formula (2) is carried out in an inert organic solvent having a boiling point of 160°–250° C. Suitable solvents are: o-dichlorobenzene, nitrobenzene, 1,2,3-trimethylbenzene, a mixture of 26.5% of diphenyl and 73.5% of diphenyl ether (®Dowtherm) or anisole. Preferred solvents are suitably o-dichlorobenzene and 1,2,3-trimethylbenzene ®Dowtherm.

The reaction to give the compounds of formula (2) may be carried out under phase transfer conditions and using a phase transfer catalyst such as tetrabutylammonium bromide, butyltriethylammonium bromide or chloride, butyltributylammonium bromide or chloride.

The hydroxy triazines of formula (2) are known, for example from A. Pinner, Chem. Ber. 23, 1919 (1890).

Compared with the process described therein, the compounds of formula (2) are obtained by the process of this invention in a one-step process without isolation of the alkyl benzimidoylcarbamate. Moreover, the hydroxyphenyl-s-triazine of formula (2) is obtained in such good purity that it may conveniently be further processed, without isolation, to a 2-(2',4'-dihydroxyphenyl)-4,6-diaryl-s-triazine of formula (1). These compounds can thus also be prepared in simple manner and in good yield by a one pot process.

The invention accordingly also relates to a process for the preparation of 2-(2',4'-dihydroxyphenyl)-4,6-diaryl-s-triazines of formula (1), which comprises reacting a benzamidine hydrohalide with an alkyl formate to 2-hydroxy-4,6-diaryl-s-triazine of formula (2) under a reduced pressure of 150–200 mbar as described above, and reacting this intermediate, without isolation, in the temperature range from 100°–150° C. with thionyl chloride in the presence of a catalytic amount of a polar solvent, and subsequently reacting the chloro-s-triazine intermediate with 1,3-dihydroxybenzene, using a Lewis acid in the presence of an inert organic solvent, to give the compound of formula (1).

The process of this invention makes it possible to prepare 2-(2',4'-dihydroxyphenyl)-4,6-diaryl-s-triazines and also the starting compounds in simple manner and in good yield.

The compounds obtained by the process of this invention find utility as UV absorbers or as starting materials for the preparation of UV absorbers.

The invention is illustrated by the following Examples.

PREPARATION OF THE STARTING MATERIALS

Example 1

47 g of benzamidine hydrochloride are dissolved in 250 ml of water and to the solution was added 80 g of a 30% solution of sodium hydroxide. With rapid stirring and gentle cooling, the 32.6 g of ethyl chloroformate are slowly run into the reaction mixture over c. 5 minutes, the temperature rising to 40°14 45° C. The reaction mixture is stirred for 1½ hours at 45°–50° C. to bring the reaction to completion. Then 150 ml of o-dichlorobenzene are run into the resultant emulsion. After stirring briefly, the o-dichlorobenzene phase is separated from the aqueous phase, heated to the boil in a flask with distillation head, and kept for 1½ hours at the boil (175°–180° C.). After cooling to room temperature, the precipitated product is isolated by filtration, washed twice with methanol and dried at 80° C. under vacuum. For purification, the product is heated for 15 minutes to the boil in 250 ml of a solution of methanol/water in the ratio 8:2 and then isolated by filtration, giving the compound of formula

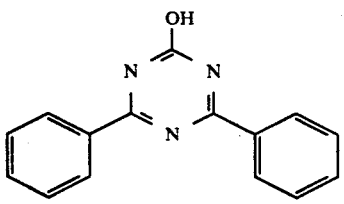

(101)

The yield of crude product after drying is 30.5 g (=81.6% of theory). The melting point after one recrystallisation is 296°–298° C.

EXAMPLE 2

412.2 g of a 38% solution of benzamidine hydrochloride in methanol are mixed with 500 ml of 1,2,3-trimethylbenzene. Then 300 ml of methanol are distilled from the mixture at 40°–50° C. under a weak vacuum. After addition of 100 ml of water and 80 g of a 50% aqueous solution of sodium hydroxide, the mixture is stirred for a further 30 minutes at 20°–30° C. To the reaction mixture are added 150 ml of water, 80 g of a 50% aqueous solution of sodium hydroxide and 1 g of tetrabutylammonium bromide. With rapid stirring (500 rpm) and cooling, 112.9 g of ethyl chloroformate are then added dropwise at 15°–20° C. over 1 hour, while keeping the pH at 8–8.5 by addition of 50% aqueous sodium hydroxide. The reaction mixture is stirred for 1 hour, then heated to 70° C. and the water is removed from the organic phase. As described in Example 1, the organic phase is heated for 2 hours to 170°–175° C., while simultaneously removing ethanol by distillation. After cooling, the precipitated product is purified with methanol/water, giving 105 g (=84.3% of theory) of the crude compound of formula (101) with a melting point of 295°–297° C. (after recrystallisation).

Example 3

157.6 g of benzamidine hydrochloride (purity: 99.4%) are stirred for 30 minutes at room temperature with 250 ml of water and 80 g of a 50% solution of sodium hydroxide. After addition of a further 30 g of sodium hydroxide solution, 112.9 g of ethyl chloroformate are added dropwise, with rapid stirring (500 rpm) and cooling, over 1 hour at 15°–20° C. The resultant crystal slurry is stirred for a further hour at room temperature. After addition of 100 ml of 1,2,3-trimethylbenzene, the slurry is heated to 85° C. and the crystalline product dissolves. The aqueous phase is separated and the organic phase is run into 400 ml of 1,2,3-trimethylbenzene at 170°–175° over 1 hour, while simultaneously distilling alcohol from the mixture. After stirring for 1 hour at 170°–175° C. and then cooling to room temperature, the precipitated product is isolated by filtration and purified as described in Example 1, giving 105.5 g of the compound of formula (101). The melting point is in the range 296°–297° C. (after recrystallisation).

Example 4

157.6 g of benzamidine hydrochloride (purity: 99.4%) are reacted with 300 ml of water, 112.9 g of ethyl chloroformate and 160 g of a 50% solution of sodium hydroxide as in Example 3(a). Then 300 ml of ®Dowtherm solvent are run into the suspension. After heating to 70° C. and separating the aqueous phase, the solvent (®Dowtherm) phase is heated to 170° C. under a vacuum of 200 mbar, while distilling ethanol and urethane from the mixture. When the reaction is complete, the precipitated product is cooled to 70° C., treated with 200 ml of methanol and then isolated by filtration at room temperature. The filter product is washed with methanol and dried at 120° C. under vacuum. The yield is 108 g (86% of theory). Analysis by thin-layer chromatography shows a pure product which does not have to be recrystallised.

PREPARATION OF THE CHLORO-S-TRIAZINE INTERMEDIATE

Example 5

24.9 g 2-hydroxy-4,6-diphenyl-s-triazine are heated to 80° C. in 175 ml of xylene (mixture of isomers). After addition of 2 ml of dimethyl formamide, 13.1 g of thionyl chloride are run in over 30 minutes. The reaction mixture is subsequently stirred for 30 minutes at 85°–90° and thereafter for 3 hours at 125°–130°. The resultant solution is concentrated to dryness by evaporation, giving 26 g (=97.1% of theory) of the compound of formula

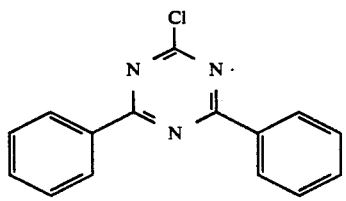

(102)

with a melting point of 139°–140°.

PREPARATION OF THE FINAL PRODUCTS

Example 6

124.6 g of 2-hydroxy-4,6-diphenyl-1,3,5-s-triazine are suspended in 600 ml of xylene (mixture of isomers) and, after addition of 3 ml of dimethyl formamide, heated to 100° C. With good stirring, 71.4 g of thionyl chloride are run in at 100°–105° C. over 1 hour. The thin suspension is stirred for 1hour at the same temperature and then heated to 125°–130° C. until it has dissolved completely. After cooling to 100° C., 100 ml of the xylene mixture is distilled from the solution. The solution is cooled to 60° C. and 73.3 g of anhydrous aluminium chloride (Merck) are added over 1 hour. The mixture is heated again to 80° C. and, with good stirring, a suspension of 66.1 g of 1,3-dihydroxybenzene in 100 ml of xylene (mixture of isomers) is added over 30 minutes. To bring the reaction to completion, the reaction mixture is stirred for a further 5 hours at 85° C. To the reaction mixture is thereafter added a mixture of 450 ml of water and 50 ml of 30% hydrochloric acid. After heating to 100° C., the xylene mixture is removed from the reaction mixture by steam distillation. The precipitated solid is isolated by filtration at 80° C., washed free of acid with hot water and dried at 80°–90° C. under vacuum. The product is purified by treatment at 90° C. with a mixture of dimethyl formamide/water in the ratio 7:3, giving 151.8 g (=88% of theory) of the compound of formula

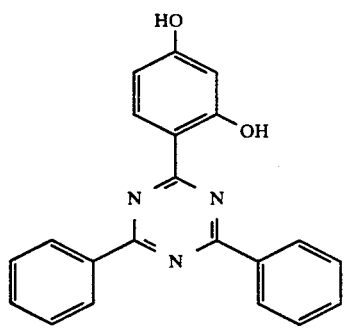

(103)

with a melting point of 272°–273°.

What is claimed is:

1. A process for the preparation of a 2-hydroxy-4,6-diaryl-s-triazine of formula (2), which comprises reacting an aqueous alkaline solution of a benzamidine hydrohalide in the temperature range from 0° to 80° C. with an alkyl halocarbonate to an alkyl benzimidoylcarbamate, adding an inert organic solvent to the resultant emulsion, and reacting the organic phase containing the alkyl benzimidoylcarbamate to give the 2-hydroxy-4,6-diaryl-s-triazine according to the reaction scheme

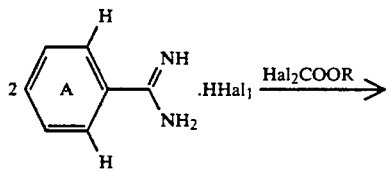

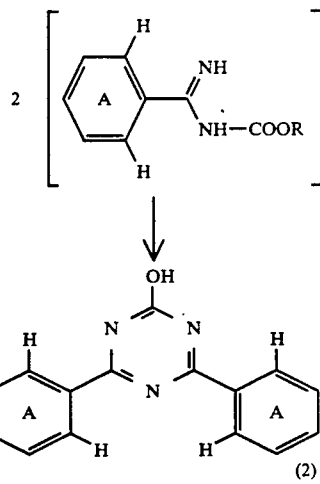

wherein $Hal_1$ and $Hal_2$ are halogen and R is $C_1$–$C_4$alkyl, and the rings A may be further substituted by halogen, hydroxy, lower alkyl, lower alkoxy or lower alkoxycarbonyl.

2. A process according to claim 1, wherein the reaction is carried out under a reduced pressure of 150–200 mbar.

3. A process according to claim 2, wherein the benzamidine hydrohalide is benzamidine hydrochloride.

4. A process according to claim 1, wherein the formate is ethyl bromoformate or ethyl chloroformate.

5. A process according to claim 1, wherein the alkaline solution of the benzamidine hydrohalide is a sodium hydroxide solution.

6. A process according to claim 1, wherein the organic solvent is a solvent having a boiling point in the range from 160°–250° C.

7. A process according to claim 6, wherein the solvent is selected from the group.

* * * * *